(12) United States Patent
Montero-Menei et al.

(10) Patent No.: US 9,579,287 B2
(45) Date of Patent: Feb. 28, 2017

(54) MICROPARTICLES SUPPORTING CELLS AND ACTIVE SUBSTANCES

(71) Applicant: INSERM, Paris (FR)

(72) Inventors: Claudia Montero-Menei, Angers (FR); Philippe Menei, Angers (FR); Jean-Pierre Benoit, Avrillé (FR); Valérie Tatard, Angers (FR); Marie-Claire Venier, Juigne-sur-Loire (FR)

(73) Assignee: INSERM (INSTITUT NATIONAL DE LA SANTE ET DE LA RECHERCHE MEDICALE), Paris (FR)

( * ) Notice: Subject to any disclaimer, the term of this patent is extended or adjusted under 35 U.S.C. 154(b) by 0 days.

(21) Appl. No.: 14/607,535

(22) Filed: Jan. 28, 2015

(65) Prior Publication Data
US 2015/0174072 A1 Jun. 25, 2015

Related U.S. Application Data

(60) Division of application No. 10/980,384, filed on Nov. 3, 2004, now abandoned, which is a continuation of application No. PCT/FR03/01377, filed on May 2, 2003.

(30) Foreign Application Priority Data

May 3, 2002 (FR) ...................................... 02 05574

(51) Int. Cl.
| A61K 9/00 | (2006.01) |
|---|---|
| A61K 9/16 | (2006.01) |
| A61K 38/18 | (2006.01) |
| A61K 38/19 | (2006.01) |

(52) U.S. Cl.
CPC ............ *A61K 9/167* (2013.01); *A61K 38/185* (2013.01); *A61K 38/193* (2013.01)

(58) Field of Classification Search
CPC ............ C12N 2531/00; C12N 2533/54; C12N 5/0629; C12N 2510/02; C12N 2510/00; C12N 2533/40; C12N 5/0068; C12N 11/04; C12N 2502/094; C12N 2502/1323; C12N 2799/022; C12N 5/0645; C12N 5/0655
USPC ...... 424/489, 443, 422, 484, 490, 93.7, 426, 424/401; 435/320.1, 325, 366, 371, 382
See application file for complete search history.

(56) References Cited

U.S. PATENT DOCUMENTS

| 4,373,027 A | 2/1983 | Berneman et al. |
|---|---|---|
| 5,830,507 A | 11/1998 | Armstrong |
| 5,846,565 A | 12/1998 | Brem et al. |
| 6,309,669 B1 | 10/2001 | Setterstrom et al. |
| 6,376,644 B1 | 4/2002 | Mao et al. |
| 7,297,538 B2 | 11/2007 | Lee et al. |
| 8,093,211 B2 * | 1/2012 | Tennenbaum ....... A61K 31/785 514/5.9 |
| 2001/0031262 A1 | 10/2001 | Caplan et al. |
| 2003/0114366 A1 | 6/2003 | Martin et al. |
| 2003/0124149 A1 * | 7/2003 | Shalaby ................ A61K 9/167 424/277.1 |
| 2003/0211083 A1 | 11/2003 | Vogel et al. |

FOREIGN PATENT DOCUMENTS

| EP | 0 030 885 A2 | 6/1981 |
|---|---|---|
| EP | 1 159 967 A1 | 12/2001 |
| JP | 4-360682 A | 12/1992 |
| JP | 5-000081 A | 1/1993 |
| JP | 9-255777 A | 9/1997 |
| JP | 11-193246 A | 7/1999 |
| JP | 2001-10961 A | 1/2001 |
| WO | 90/10018 A1 | 9/1990 |
| WO | 98/28357 A1 | 7/1998 |
| WO | 98/51812 A2 | 11/1998 |
| WO | 98/52605 A1 | 11/1998 |
| WO | 02/04001 A2 | 1/2002 |

OTHER PUBLICATIONS

Matthew W. Davis et al., "Toward Development of an Implantable Tissue Engineered Liver," Biomaterials, 1996, vol. 17, No. 3, pp. 365-372.
Z.J. Gong et al., "Hepatitis B virus infection in microcarrier-attached immortalized human hepatocytes cultured in molecularporous membrane bags: a model for long-term episomal replication of HBV," Journal of Viral Hepatitis, 1998, vol. 5, pp. 377-387.
Melissa J. Mahoney et al., "Transplantation of brain cells assembled around a programmable synthetic microenvironment," Nature Biotechnology, Oct. 2001, vol. 19, pp. 934-939.
Bao Gang Peng et al., "Autologous Fixed Tumor Vaccine: A Formulation with Cytokine-microparticles for Protective Immnity against Recurrence of Human Hepatocellular Carcinoma," Jpn. J. Cancer Research, Apr. 2002, vol. 93, No. 4, pp. 363-368.
Francesca Aloisi et al., Regulation of T-cell responses by CNS antigen-presenting cells: different roles for microglia and astrocytes, Immunology Today, © 2000 Elsevier Science Ltd., 21: 141-147.
Jean-Pierre Benoit et al., Development of microspheres for neurological disorders: From basics to clinical applications, Journal of Controlled Release, © 2000 Elsevier Science B.V., 65: 285-296.

(Continued)

*Primary Examiner* — Janet Epps-Smith
(74) *Attorney, Agent, or Firm* — Whitham, Curtis & Cook, P.C.

(57) ABSTRACT

A method of repairing tissue includes implanting into a patient a therapeutically effective amount of a pharmaceutical composition including microparticles including a biodegradable, biocompatible material having cells of interest or fragments thereof adhered to at least a portion of a surface; and at least one substance active on the cells or their environment upon implantation of the microparticles in a patient associated with the material wherein the substances is released in a controlled or extended manner.

9 Claims, 2 Drawing Sheets

(56) References Cited

OTHER PUBLICATIONS

Cesario V. Borlongan et al., Intrastriatal Transplantation of Rat Adrenal Chromaffin Cells Seeded on Microcarrier Beads Promote Long-Term Functional Recovery in Hemiparkinsonian Rats, Experimental Neurology, © 1998 by Academic Press, 151: 203-214, Article No. EN986790.

Noel G. Carlson et al., Inflammatory Cytokines IL-1α-IL-1β, IL-6, and TNF-α Impart Neuroprotection to an Excitotoxin Through Distinct Pathways, The Journal of Immunology, © 1999 by The American Association of Immunologists, 163: 3963-3968.

B.D. Cherksey et al., Adrenal Chromaffin Cells on Microcarriers Exhibit Enhanced Long-Term Functional Effects When Implanted Into the Mammalian Brain, Neuroscience, © 1996 by Elsevier Science Ltd., vol. 75, No. 2, pp. 657-664.

Isao Date et al., Neural Transplantation and Trophic Factors in Parkinson's Disease: Special Reference to Chromaffin Cell Grafting, NGF Support from Pretransected Peripheral Nerve, and Encapsulated Dopamine-Secreting Cell Grafting, Experimental Neurology, © 1996 by Academic Press, Inc., 137: 333-344.

Frédéric Dehaut et al., Differential behaviour of PC12 cells grafted into rat hippocampus and striatum, Neuroscience Letters, © 1993 Elsevier Scientific Publishers Ireland Ltd., 153: 41-44.

Achilles A. Demetriou et al., Survival, Organization, and function of microcarrier-attached hepatocytes transplanted in rats, Proc. Natl. Acad. Sci. USA, Oct. 1986 Medical Sciences, vol. 83, pp. 7475-7479.

Mia Emgård et al., Patterns of Cell Death and Dopaminergic Neuron Survival in Intrastriatal Nigral Grafts, Experimental Neurology, © 1999 by Academic Press, 160: 279-288.

Paul T. Golumbek et al., Controlled Release, Biodegradable Cytokine Depots: A New Approach in Cancer Vaccine Design, Cancer Research, 53: 5841-5844, Dec. 15, 1993.

Emmanuel O. Junard et al., Long-Term Administration of Mouse Nerve Growth Factor to Adult Rats with Partial Lesions of the Cholinergic Septohippocampal Pathway, Experimental Neurology, © 1990 by Academic Press, Inc., 110: 25-38.

U. Kneser et al., Interaction of hepatocytes and pancreatic islets cotransplanted in polymeric matrices, Virchows Arch, © Springer-Verlag 1999, 435: 125-132.

Olle Lindvall, Neural Transplantation, Cell Transplantation, © 1995 Elsevier Science Ltd., vol. 4, No. 4, pp. 393-400.

Thomas J. Mahalik et al., Programmed Cell Death in Developing Grafts of Fetal Substantia Nigra, Experimental Neurology, © 1994 by Academic Press, Inc., 129: 27-36.

Melissa J. Mahoney et al., Millimeter-scale positioning of a nerve-growth-factor source and biological activity in the brain, Proc. Natl. Acad. Sci. USA, Apr. 1999 Medical Scients, vol. 96, pp. 4536-4539.

P. Menei et al., Intracerebral Graft of a Chromaffin Cell Line: Immunologic aspects and role of the nerve growth factor in the survival and differentiation of the graft, Neurochirurgie, © Masson, Paris, 1989, 35: 158-163 (pp. 158 and 163 missing).

P. Menei et al., Biological Complications and Risks of Neuronal Grafts, Neurochirurgie, © Masson, Paris, 1991, 37: 364-376 (p. 364 missing).

P. Menei et al., Intracerebral grafts in Parkinson's disease, La Presse Medicate, © Masson, Paris, Mar. 23, 1991, vol. 20, No. 11, pp. 513-517.

P. Menei et al., Biodegradation and brain tissue reaction to poly(D,L-lactide-co-glycolide) microspheres, Biomaterials, © 1993 Butterworth0Heinemann Ltd., vol. 14, No. 6, pp. 470-478.

Philippe Menei, M.D., et al., Drug Targeting into the Central Nervous System by Stereotactic Implantation of Biodegradable Microspheres, Neurosurgery, vol. 34, No. 6, Jun. 1994, pp. 1058-1064.

P. Menei et al., Fate and biocompatibility of three types of microspheres implanted into the brain, Journal of Biomedical Materials Research, © 1994 John Wiley & Sons, Inc., vol. 28, pp. 1079-1085.

P. Menei et al., Drug delivery into the brain using implantable polymeric systems, S.T.P. Pharma Sciences, 1997, 7: 53-61.

Philippe Menei et al., Schwann cells genetically modified to secrete human BDNF promote enhanced axonal regrowth across transected adult rat spinal cord, European Journal of Neuroscience, © European Neuroscience Association, 1998, vol. 10, pp. 607-621 (pp. 614 and 615 missing).

Philippe Menei, M.d., Ph.D., et al., Local and Sustained Delivery of 5-Fluorouracil from Biodegradable Microspheres for the Radiosensitization of Glioblastoma: A Pilot Study, Cancer, © 1999 American Cancer Socieity, Jul. 15, 1999, vol. 86, No. 2, pp. 325-333.

P. Menei et al., Intracerebral Implantation of NGF-Releasing Biodegradable Microspheres Protects Striatum against Excitotoxic Damage, Experimental Neurology, © 2000 by Academic Press, 161: 259-272.

Matthew F. Mescher et al., Immunotherapy of Established Murine Tumors with Large Multivalent Immunogen and Cyclophosphamide, Journal of Immunotherapy, © 1996 Lippincott-Raven Publishers, Philadelphia, 19(2): 102-112.

Matthew F. Mescher et al., Stimulation of Tumor-Specific Immunity Using Tumor Cell Plasma Membrane Antigen, Methods: A Companion to Methods in Enzymology, © 1997 by Academic Press, 12: 155-164, Article No. ME970466.

Claudia N. Montero et al., Rescue of Lesioned Septal Cholinergic Neurons by Nerve Growth Factor: Specificity and Requirement for Chronic Treatment, The Journal of Neuroscience, © 1988 Society for Neuroscience, Aug. 1988, 8(8): 2986-2999.

Claudia N. Montero et al., Intraventricular Nerve Growth Factor Administration Prevents Lesion-Induced Loss of Septal Cholinergic Neurons in Aging Rats, Neurobiology of Aging, © Pergamon Press plc, 1989, vol. 10, pp. 739-743.

Claudia N. Montero-Meni et al., Pure Schwann cell suspension grafts promote regeneration of the lesioned septo-hippocampal cholinergic pathway, Brain Research, Elsevier Science Publishers B.V., 1992, 570: 198-208.

Jacob Mullerad et al., Macrophage Activation for the Production of Immunostimulatory Cytokines by Delivering Interleukin 1 Via Biodegradable Microspheres, Cytokine, vol. 12, No. 11, Nov. 2000, pp. 1683-1690.

Ryusuke Nakaoka et al., Potentiality of gelatin microsphere as immunological adjuvant, Vaccine, © 1995 Elsevier Science Ltd, 13: 633-661.

Harald Neumann et al., Neurotrophins inhibit major histocompatibility class II inducibility of microglia: Involvement of the p75 neurotrophin receptor, Proc. Natl. Acad. Sci. USA, © by The National Academy of Sciences, May 1998 Neurobiology, vol. 95, pp. 5779-5784.

Jean-Manuel Péan et al., NGF release from poly(D,L-lactide-co-glycolide) microspheres. Effect of some formulation parameters on encapsulated NGF stability, Journal of Controlled Release, © 1998 Elsevier Science B.V., 56: 175-187.

Jean-Manuel Péan et al., Why Does PEG 400 Co-Encapsulation Improve NGF Stability and Release from PLGA Biodegradable Microspheres?, Pharmaceutical Research, © 1999 Plenum Publishing Corporation, vol. 16, No. 8, pp. 1294-1299.

Jean-Manuel Péan et al., Intraseptal implantation of NGF-releasing microspheres promote the survival of axotomized cholinergic neurons, Biomaterials, © 2000 Elsevier Science Ltd., 21: 2097-2101.

Dean K. Pettit et al., Characterization of Poly(glycolide-co-D,L-lactide)/Poly(D,L-lactide) Microspheres for Controlled Release of GM-CSF, Pharmaceutical Research, © 1997 Plenum Publishing Corporation, vol. 14, No. 10, pp. 1422-1430.

Joy Rogers et al., Augmentation of In Vivo Cytotoxic T Lymphocyte Activity and Reduction of Tumor Growth by Large Multivalent Immunogen, The Journal of Immunology, © 1992 by The American Association of Immunologists, Jul. 1, 1992, vol. 149, No. 1, pp. 269-276.

Samuel Saporta et al., Microcarrier Enhanced Survival of Human and Rat Fetal Ventral Mesencephalon Cells Implanted in the Rat Striatum, Cell Transplantation, © 1997 Elsevier Science Inc., vol. 6, No. 6, pp. 579-584.

(56) References Cited

OTHER PUBLICATIONS

J. Sautter et al., Implants of Polymer-Encapsulated Genetically Modified Cells Releasing Glial Cell Line-Derived Neurotrophic Factor Improve Survival, Growth, and Function of Fetal Dopaminergic Grafts, Experimental Neurology, © 1998 by Academic Press, 149: 230-236, Article No. EN976718.

Christoph Scheicher et al., Uptake of Bead-Adsorbed Versus Soluble Antigen by Bone Marrow Derived Dendritic Cells Triggers Their Activation and Increases Their Antigen Presentation Capacity, *Dendritic Cells in Fundamental and Clinical Immunology*, Plenum Press, New York, 1995, vol. 2, pp. 253-255.

Christoph Scheicher et al., Uptake of microparticle-adsorbed protein antigen by bone marrow-derived dendritic cells results in up-regulation of interleukin-1α and interleukin-12 p40/p35 and triggers prolonged, efficient antigen presentation, Eur. J. Immunol, © VCH Verlagsgesellschaft mbH, D-69451 Weinheim, 1995, 25: 1566-1572.

Paul J.L.M. Strijbos et al., Interleukin-1β Attenuates Excitatory Amino Acid-Induced Neurodegeneration in vitro: Involvement of Nerve Growth Factor, The Journal of Neuroscience, © 1995 Society for Neuroscience, May 1995, 15(5): 3468-3474.

Anje A. te Velde et al., Three Different Hepatocyte Transplantation Techniques for Enzyme Deficiency Disease and Acute Hepatic Failure, *Artif Organs*, 1992, vol. 16, No. 5, pp. 522-526.

Nina Törnqvist et al., Implantation of Bioactive Growth Factor-Secreting Rods Enhances Fetal Dopaminergic Graft Survival, Outgrowth Density, and Functional Recovery in a Rat Model of Parkinson's Disease, Experimental Neurology, © 2000 by Academic Press, 164: 130-138.

James Varani et al., Use of recombinant and synthetic peptides as attachment factors for cells on microcarriers, *Cytotechnology*, © 1993 Kluwer Academic Publishers, The Netherlands, 13: 89-98.

N. Venkataprasad et al., Induction of cellular immunity to a mycobacterial antigen adsorbed on lamellar particles of lactide polymers, Vaccine, © 1999 Elsevier Science Ltd., 17: 1814-1819.

Joëlle Veziers et al., Analysis of brain biocompatibility of drug-releasing biodegradable microspheres by scanning and transmission electron microscopy, *J. Neurosurg.*, Sep. 2001, vol. 95, pp. 489-494.

M. Voigt, M.D. et al., Cultured Epidermal Keratinocytes on a Microspherical Transport System Are Feasible to Reconstitute the Epidermis in Full-Thickness Wounds, Tissue Engineering, 1999, vol. 5, No. 6, pp. 563-572.

Rongtai Wei et al., Neurotrophins and the anti-inflammatory agents interleukin-4 (IL-4), IL-10, IL-11 and transforming growth factor-β1 (TGF-β1) down-regulate T cell costimulatory molecules B7 and CD40 on cultured rat microglia, Journal of Neuroimmunology, © 1999 Elsevier Science B.V., 95: 8-18.

Kathryn J. Wood et al., Gene therapy in transplantation, Current Opinion in Molecular Therapeutics, © PharmaPress Ltd., 2001, 3(4): 390-398.

David M. Yurek et al., BDNF Enhances the Functional Reinnervation of the Striatum by Grafted Fetal Dopamine Neurons, Experimental Neurology, © 1996 by Academic Press, Inc., 137: 105-118, Article No. 0011.

W. Michael Zawada et al., Growth factors improve immediate survival of embryonic dopamine neurons after transplantation into rats, Brain Research, © 1998 Elsevier Science B.V., 786: 96-103.

\* cited by examiner

MICROPARTICLES SUPPORTING CELLS AND ACTIVE SUBSTANCES

RELATED APPLICATION

This is a divisional of U.S. Ser. No. 10/980,384, filed Nov. 3, 2004, which is a continuation of International Application No. PCT/FR03/01377, with an international filing date of May 2, 2003 (WO 03/092657, published Nov. 13, 2003), which is based on French Patent Application No. 02/05574, filed May 3, 2002.

TECHNICAL FIELD

This disclosure pertains to the field of the preparation and transplantation of cells useful in the framework of cell therapy for tissue repair or gene transfer, or for vaccination. More specifically, the disclosure relates to microparticles based on a biocompatible, biodegradable material carrying the cells of interest or fragments thereof and growth factors or cytokines.

BACKGROUND

Cell therapy by graft of autologous or nonautologous cells constitutes a major therapeutic tool which is at present essentially developed in hemobiology, but should be applicable to other specialties based on the knowledge acquired regarding stem cells and their identification in most tissues, ranging from muscle to the central nervous system. The increasing identification and characterization of cytokines and growth factors allow us to envisage the possibility of in vitro and/or in vivo control of the proliferation and differentiation of these cells and the modulation of their tissue environment (immunologic rejection phenomena, angiogenesis). Despite these advances in cell biology, the clinical development of cell grafts remains limited at present, notably because of the low survival rate of the implanted cells which can be linked to a nonspecific mortality (cell death by necrosis or apoptosis) due to the procedures employed for collection, storage, transformation and administration or to an immunologic rejection (in allografts and xenografts), i.e., the absence of integration in the host tissue.

It has been proposed to use nonbiodegradable microbeads on which the cells adhere thereby functioning as transporters or microcarriers to reduce this cellular mortality. For example, the survival and functioning of hepatocytes were improved when such cells were grafted/adhered to glass or dextran (Cytodex®) microbeads (Demetriou et al., 1986; Te Velde et al., 1992). This strategy has made it possible to obtain more promising results than with microencapsulated hepatocytes.

More recently, these same microbeads have been used for cultivating and grafting human keratinocytes to reconstitute a cutaneous cover in the nude mouse (Voigt et al., 1999). This approach has also been used for grafting neurochromaffins or dopaminergic embryonic neurons in a murine model of Parkinson's disease. In this model, the survival of the transplanted cells in the striatum is greatly increased when they are first adhered to glass or dextran microparticles, thereby enabling behavioral improvement of the animals (Cherskey et al., 1996; Saporta et al., 1997; Borlongan et al., 1998).

It has also been observed (Saporta et al., 1997) that human fetal cells adhered on dextran microbeads survive for at least three months without immunosuppressant treatment, whereas such cells without microparticles are rapidly rejected.

Another more recent approach enabling augmentation of the survival of grafted cells is the administration of growth factors in association with the graft. These proteins, which can act on proliferation, differentiation, activation and survival of the cells, constitute a major contribution to the field of cell grafts. Although it is now possible to have available human recombinant growth factors, their administration represents a challenge because these products have a short half-life and do not cross certain biological barriers. They moreover have a pleiotropic action which can be the cause of undesirable side effects. The presently developed modes of administration are not completely satisfactory and/or applicable in clinical practice.

One of the first modes of administration proposed grafting cells in a suspension containing growth factor. Although this approach is simple, it does not enable long-term action on the cells. A second mode of administration consists of co-transplanting a tissue identified as producing the selected growth factor, e.g., peripheral nerve-chromaffin cell co-grafts (Date et al., 1996) or hepatocyte-islets of Langerhans co-grafts (Kneser et al., 1999). The sometimes limited survival of such co-grafts and the inability to control the doses of growth factors considerably limits this strategy. Progress made in molecular biology now allows for the production of genetically modified cells producing a growth factor which can be used in co-grafts or in grafts as usually defined (Menei et al., 1998; Wood and Prior, 2001). Nevertheless, this approach remains limited by ethical problems, biological risk and control of the released doses. Grafts of nerve cells have been reported such as PC12 neuroendocrine cells (Menei et al., 1989; Dehaut et al., 1993), and normal Schwann cells or Schwann cells genetically modified to produce a neurotrophic factor (Montero-Menei et al., 1992; Menei et al., 1998).

There have also been reports of biodegradable microparticles releasing neuroactive molecules in a controlled and prolonged manner (Menei et al., 1997; Benoit et al., 1999). These microspheres are constituted of a biopolymer of the poly(lactic acid-glycolic co-acid) (PLGA) type. They are biocompatible with nerve tissue and totally degraded in several months (Menei et al., 1993; 1994b; Véziers et al., 2000). Their size of several tens of microns allows stereotactic implantation in the brain at the level of their pharmacological target using the same microsyringes as for cell implantations (Menei et al., 1994a). They were used successfully in a phase I clinical study for the interstitial chemotherapy of brain tumors (Menei et al., 1999).

Microspheres releasing proteins, in particular growth factors and cytokines, have also been developed. Nerve growth factor (NGF) is a substance of interest because it was among the earliest characterized. There have been descriptions of microspheres that can release NGF over at least two months (Péan et al., 1998; Péan et al., 1999). Their therapeutic value was demonstrated on two animal models of neurodegenerative diseases: the murine model of Alzheimer's disease (Péan et al., 2000) and the murine model of Huntington's chorea (Menei et al., 2000).

In the field of tumors, PLGA microspheres have been formulated which are capable of releasing immunostimulant cytokines after intratumoral implantation (Mullerad et al. 2000; Pettit et al., 1997). The use of biodegradable microspheres for the release of cytokines in the framework of antitumor vaccine was therefore proposed (Golumbek et al., 1993). However, in that study the microspheres were simply mixed with the cells immediately prior to injection. In fact, the preparation of vaccine constituted of microspheres coated by bacterial antigens or membrane vesicles had already been proposed, but without the microspheres having the ability to release immunostimulant molecules (Mescher and Rogers, 1996; Mesher and Savelieva, 1997).

SUMMARY

We provide microparticles including a biodegradable, biocompatible material having at least a portion of its surface adapted to adhere to cells of interest or fragments thereof, and at least one substance active on the cells or their environment upon implantation of the microparticles in a patient associated with the material, wherein the substance is released in a controlled and/or extended manner.

We also provide a pharmaceutical composition for tissue repair or gene transfer including the microparticles.

We further provide an antitumor vaccine including the microparticles.

We still further provide a method of repairing tissue including administering a therapeutically effective amount of the pharmaceutical composition to the patient.

We also further provide a method of vaccinating against tumors including administering an effective amount of the vaccine to the patient.

BRIEF DESCRIPTION OF THE DRAWINGS

Other advantages and characteristics of the disclosure will become apparent from the examples below pertaining to the preparation and use of MPAs in the field of neurotransplantation in which reference will be made to the attached drawings.

DETAILED DESCRIPTION

Figure 1:
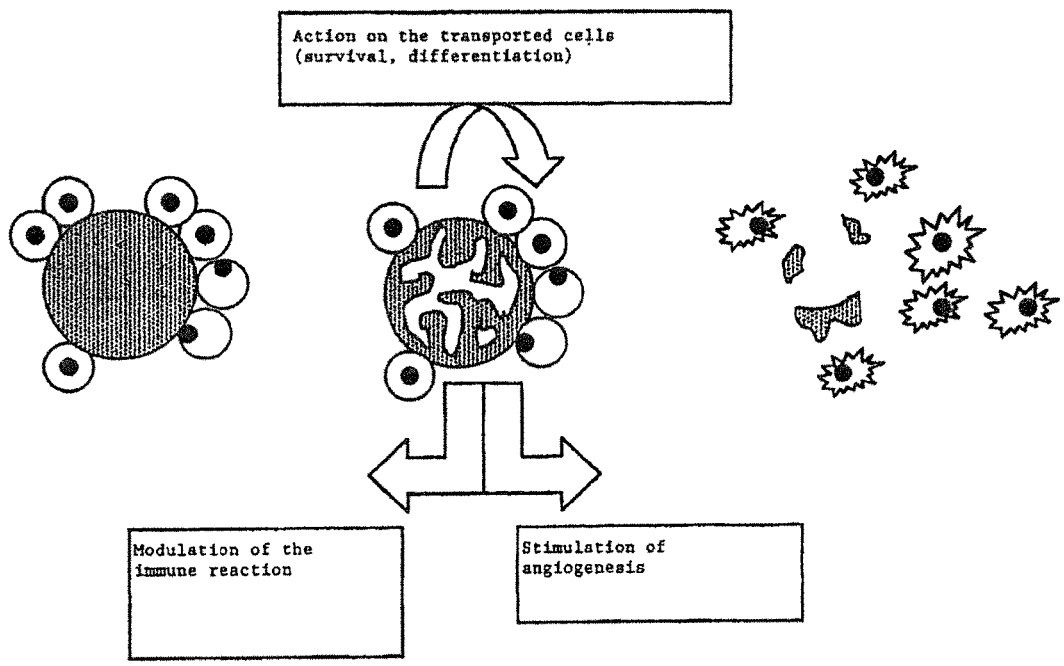
FIG. 1 is a schematic representation of MPAs.

This disclosure provides a combination of cells (or cell fractions) and substances active on these cells such as growth factors or cytokines, at the level of the same microparticles for the grafting of cells in cell therapy or vaccination.

We developed pharmacologically active microcarriers, designated below as "MPAs," which release growth factors in a prolonged and controlled manner. These microparticles of several tens of microns in diameter comprise biodegradable, biocompatible polymers enabling the adherence of cells or cell fragments due to the intrinsic properties of the polymer or of a coating which can be biologically active. MPAs do not present a biological risk and are remarkable because, among other things:

Their function as a support for the culture of cells (or their fragments). The preferential adhesion of the cells to be grafted on the microparticles allows their in vitro preparation as well as transformation without the necessity of using for their collection proteolytic enzymes of animal origin which is not recommended because of obvious health safety reasons.

They function as a support for grafted cells (or cell fragments) and degrade without toxicity after implantation, not interfering with integration of the grafted cells (or their fragments).

They release one or more growth factors or cytokines during a programmed or specified duration of time and at a determined dosage.

They promote the survival and differentiation of the grafted cells, modify their microenvironment, as well as their integration in the host tissue.

We thus provide microparticles based on a biocompatible, biodegradable material that carries on their surface the cells of interest or fragments thereof and they comprise molecules of at least one substance active on the cells or their environment upon implantation of the microparticles, the molecules being released by the microparticles in a controlled and/or prolonged manner.

Our compositions and methods can be implemented in many ways in which the molecules of at least one active substance are on the surface of and/or incorporated in the microparticles. Incorporation of the active molecule can be implemented during the encapsulation process and/or after formation of the particles. The matrix can be porous to varying degrees with an essentially spherical form according to operating conditions.

The microparticles comprise a biodegradable, biocompatible polymer or copolymer. Such a polymer or copolymer may be, e.g., at least one selected from among the group comprising poly($\alpha$-hydroxyacids) such as the polylactides, coglycolides polylactides, polyesters such as poly $\epsilon$-caprolactones, poly(orthoesters), poly(phosphazenes), PLGA and mixtures thereof. The polymer may preferably be selected from among polylactides.

The microparticles have a diameter between about 1 and about 500 μm, advantageously between about 10 and about 500 μm. The MPAs are able to adapt the size of the microparticles as a function of the adhered cells.

Adhesion of the cells on the microparticles is enabled by inherent properties of the polymer and/or by a coating with a compound or mixture of compounds enabling adhesion of the cells and which can be biologically active. Thus, we may use synthetic polymer enabling cellular adhesion by their physicochemical properties, or synthetic copolymers on the molecules from which are grafted the RGD sequences or lysine (Varani et al., 1993). As examples of compounds for coating microparticles enabling adhesion of cells, we can cite at least those selected from the group comprising poly-D-lysine, poly-L-lysine, polyornithine, polyethylene amine or other synthetic or non-synthetic molecules belonging to the extracellular matrix such as fibronectin-like agent, or mixtures thereof.

The microparticles comprise molecules of at least one substance active on the cells or the environment of these cells upon grafting. There are various methods to encapsulate these molecules. We can cite a method of double emulsion or other physicochemical, mechanical or chemical process. It is also possible to employ a simple inhibition of the microparticles with the molecules to affix them on the surface of the microparticles. The microparticles release the molecules of this substance in a controlled and/or prolonged manner.

The MPAs are useful for preparing pharmaceutical compositions useful in cell therapy for tissue repair or gene transfer. The cells of interest affixed to the surface of the microparticles can vary according to the type of graft desired. For example, they can be adult autologous cells, embryonic cells, optionally transformed cell lines of stem cells or the like. Such cells can be used in different pathologies requiring cell therapy. This is, for example, the case of grafts of hepatocytes and islets of Langerhans. In the case of neurotransplantation, this can involve a PC12 cell line capable of secreting dopamine and of differentiating itself into sympathetic-like neurons under the effect of NGF.

As examples, we can also cite grafting of cells for repair of the liver, the myocardium and the central nervous system, grafting of islets of Langerhans for treatment of diabetes and grafting of bone marrow cells in hemopathies, adult cells, embryonic cells, optionally transformed cell lines, stem cells, genetically modified cells, cells producing defective recombinant viruses for their replication, hepatocytes, islets of Langerhans, nerve cells, muscle cells, hemopoietic cells and bone cells. This can therefore involve cells enabling in vivo gene transfer such as cells containing a transgene and cells producing defective recombinant viruses for their replication which will infect the neighboring cells of the host. These cells are often obtained from animal lines and the xenogenic immune reactions prevent their survival and thus their long-term function. The use of MPAs releasing an immunomodulator and/or a factor promoting the survival of these cells makes it possible to prolong their function over time. To the contrary, the MPA can release at a selected moment a molecule that is toxic to the transported cell, thereby programming/causing its death and its elimination.

The molecules of the substances incorporated within or on the surface of the MPAs are thus advantageously growth factors, cytokines, hormones, molecules of adherence or of the extracellular matrix known for their action on the transported cells or their tissue environment. As examples, we can cite growth factors, cytokines, immunomodulators or factors acting on cell differentiation, especially those selected from the group comprising neutrophins such as NGF, BNDF, NT-3 and the like, TGFβs, the GDNF family, FGFs, EGF, PDGF, interleukins such as IL-1, IL-2, the chemokines, retinoic acid, erythropoietin, and the like, or mixtures thereof.

The molecules released by the microparticles alone or in combination with the coating compound for the adhesion of the cells promotes the survival of the cells, their function or orient the differentiation of stem cells to a determined phenotype. They can also modify the tissue environment by diminishing the immune reactions and rejection or by promoting integration by augmenting angiogenesis. These molecules can also serve to control the expression of a gene present in a genetically modified cell and which is under the control of a promoter responding to these molecules.

The disclosure thus also may use microparticles based on a biodegradable, biocompatible material to prepare a pharmaceutical composition intended for tissue repair or gene transfer, in which the microparticles comprise on their surface the cells of interest and comprise molecules of at least one substance active on the cells or their environment upon implantation of the microparticles, the molecules being released by the microparticles in a controlled and/or prolonged manner.

The MPAs may also be used to prepare vaccines particularly for antitumor vaccination. This new approach in cancer treatment uses autologous tumor cells obtained from primoculture of the patient's tumor as the source of antigen. These cells can be genetically modified to release a pro-inflammatory cytokine. The MPAs can play this role without passing through the phase of transfection and selection which lengthens the procedure.

However, one value of the MPAs is that, due to their surface properties, they can also transport not only cells, but also cell fragments preferably covered by cytoplasmic membrane or protein extract or mRNA or DNA. Representative examples include but are not limited to fragments of apoptotic bodies, exosomes or membrane vesicles obtained from tumor primoculture. Apoptotic bodies are readily obtained by the action of Na butyrate, by thermal treatment of cells followed by UV B irradiation. Membrane vesicles are obtained by cellular fragmentation followed by separation by centrifugation in a biphasic system. The value of apoptotic bodies or membrane vesicles is that they can be produced in large quantities from a tumor sample, whereas autologous cells require a phase of culture and expansion which considerably delays treatment.

In this application for vaccination, the MPAs incorporate or comprise on their surface molecules one or more pro-inflammatory cytokines or adjuvant stimulating the action of dendritic cells and the antitumor T response. We can cite as non-limiting examples of such substances those selected from the group comprising Freund's adjuvant, GM-CSF, IL12, IL4 and IL18.

The value of MPAs for vaccines is remarkable in the sense that the immunogenic character results not only in the association of the membrane antigen and the prolonged release of cytokine, but also in the presentation of the antigen on a microparticle system. This is an advantageous mode of presentation for the recognition of the antigen by dendritic cells. This nonspecific immune stimulation or the adjuvant role of the microparticles has been demonstrated over a considerable period of time (Nakaoka et al., 1995; Scheicher et al., 1995a, 1995b; Venkataprasaed et al., 1999).

The disclosure thus also comprises microparticles based on a biodegradable, biocompatible material for preparing a pharmaceutical vaccine composition, more specifically an antitumor composition, in which the microparticles contain on their surface the cells of interest or fragments thereof and comprise molecules of at least one substance active on the cells or their environment upon implantation of the microparticles, the molecules being released by the microparticles in a controlled, prolonged manner.

Example 1

General Presentation of MPAs for Cell Grafts

The non-limiting examples below pertain to the field of neurotransplantation (grafts of nerve cells in the central nervous system). Biocompatible, biodegradable MPAs of a diameter of 60 μm were prepared. They were constituted of PLGA and coated with a fine layer of synthetic adherence molecules (poly-D-lysine and fibronectin-like agent) and release NGF, a neurotrophic factor, on a continuous basis (for at least 15 days). Cells responding to NGF such as the PC12 cell line capable of secreting dopamine and of differentiating itself into sympathetic-like neurons under the effect of this factor were used. The efficacy of these MPAs was evaluated in vivo successfully using an animal model of Parkinson's disease.

Neurotransplantations began clinically in the 1980s essentially in the context of Parkinson's disease (Menei et al., 1991a, 1991b). They continue at present in the form of clinical research and remain essentially limited by the availability of cells to be grafted (embryonic cells) and the low survival rate of the cells after implantation (5 to 10%). Recent studies have shown that most of the neurons die in the first week after transplantation, probably due to a lack of trophic support, of neuron connections and a limited vascularization (Emgard et al., 1999; Mahalik et al., 1994; Zawada et al., 1998). It was demonstrated that neurotrophic factors administered in parallel with the grafted cells improved their survival. They also acted on their differentiation and the development of synapses, thereby aiding their better integration (Mahoney et al., 1999; Sautter et al., 1998; Yurek et al., 1996). These factors can also act in a beneficial manner on the environment of the grafted cells by modifying the inflammatory and cellular reaction (Wei et al., 1999).

1) Selection of the Growth Factor

NGF was initially selected because it is a trophic factor that has multiple advantages in the context of neurotransplantation. In addition to its neurotrophic action, it can protect in a nonspecific manner against the excitotoxicity responsible for an early mortality of the grafted cells (Strijbos and Rothwell, 1995; Carlson et al., 1999). NGF moreover has a potential value in the context of graft rejections. It diminishes the expression on microglial cells of the immunologic molecules essential for the activation of T cells in the central nervous system (Neumann et al., 1998; Wei and Jonakait, 1999; Aloisi et al., 2000) thereby enabling the prevention of rejection and the establishment of a local immunotolerance.

2) Selection of the Cells

The chromaffin cells of the medullar-suprarenal have been conventionally used for cell grafts in the context of Parkinson's disease. Cells of the PC12 line were therefore used because they are relatively easy to culture. These cells synthesize and release dopamine. Furthermore, under the action of NGF, they stop proliferation and differentiate themselves into sympathetic-like neurons. PC12 cells also constitute a good model for determining the production conditions of microcarriers because they do not have natural adherence properties and only adhere to surfaces coated by molecules promoting adherence.

The clinical development of embryonic cell grafts remains limited by ethical problems. It is therefore necessary at present and in the future to envisage other sources such as neural stem cells or mesenchymal stem cells of the bone marrow (MSC). These latter cells that can be readily collected in humans, are capable of differentiating themselves in vitro, in accordance with culture conditions, into osteoblasts, chondrocytes, myocytes, adipocytes or neural stem cells. Thus, MSCs differentiated into neural stem cells by basic FGF express the high affinity NGF receptor (trkA) and can be used in the framework of this disclosure.

3) Selection of the MPAs

A preferred size in this application is on the order of about 60 µm. A smaller size has an insufficient surface for allowing adherence of an acceptable number of cells. However, the microspheres should not have too large a diameter to be resorbed without difficulty and to be readily administered via a needle.

The PLGA microparticles were coated with fibronectin-like agent and poly-D-lysine for cell adhesion. The use of synthetic molecules not of animal origin is indispensable for future clinical application. These coated microspheres enable in vitro a continuous release of NGF during at least fifteen days. To study in vivo the effect of the pharmacologically active microcarriers, they were implanted in the rat striatum after total dopaminergic denervation by a neurotoxic agent (parkinsonian rat). After implantation, the PC12 cells remained adhered to the blank microparticles (without active product) or those releasing NGF. On the animals treated with the microcarriers releasing NGF, the PC12 cells were differentiated and had prolongations probably in response to the release of NGF. This differentiation was accompanied by behavioral tests (rotation test).

PC12 cells were used in this study to improve the MPAs. However, other cells can be used. Grafts of cells of embryonic origin were studied in animal models of neurodegenerative diseases. These studies led to the implementation of clinical trials in Parkinson's disease and Huntington's chorea. However, the modest effects of these grafts in relation to a high mortality of the grafted cells led to a rethinking of the methodology (Lindvall, 1997). In the framework of Parkinson's disease and grafts of dopaminergic embryonic neurons, studies showed that the exposure of these cells to GDNF (Tornqvist et al., 2000) or the use of microcarriers (Saporta et al., 1997) increased their survival. Microparticles releasing GDNF can also be prepared to promote grafting of embryonic dopaminergic neurons and study their efficacy in the rat.

Example 2

Preparation of PC12/NGF MPAs

1) Preparation of the Microparticles

The microparticles were produced by double emulsion (H/L/H) evaporation/extraction of solvent.

The aqueous phase was constituted of 60 µl of citrate buffer (16 mM, pH 6), 2.5 mg of HSA (or other molecule having a surface-active power), 90 µl of PEG 400 and 100 µg of NGF. 50 mg-100 mg of PLGA 37.5/25 (poly D,L-lactide-co-glycolide, Mw 21,000 Da, I=1.7) or another biocompatible, biodegradable polymer were dissolved in 2 ml of an organic solution constituted of 75% of dichloromethane and 25% acetone. The primary emulsion was made from these two phases by sonication at 0-4° C. (15 s, 5-6 W). This primary emulsion was added under mechanical agitation (200 rpm) to 30-150 ml of a polyvinyl alcohol solution (0.8-4.5%, 4-8° C.) containing 10% (W/V) of NaCl containing 0 to 2% of dichloromethane. Agitation was maintained for 1 to 7 minutes. The secondary emulsion was then poured into 400 ml of a 10% aqueous solution of NaCl under magnetic stirring (25-50 minutes). The aqueous extraction phase can be added in parts to the secondary emulsion. The microparticles were then filtered (0.45 µm, HVLP, Millipore), washed 5 times with 100 ml of distilled water then lyophilized and stored at +4° C.

The encapsulation yield was on the order of 85% but, depending on the manufacturing conditions, it can reach 97% (Péan et al., 1998).

2) Coating the Microparticles

Coating of the microparticles with a combination of fibronectin-like agent (16 µg/ml) with poly-D-lysine (12 µg/ml) constitutes the condition enabling adherence and an optimal differentiation of the PC12 cells.

The conditions for coating the microparticles (agitation velocity and time) were perfected by agitation of the microsphere suspension in the presence of fibronectin-like agent and poly-D-lysine. After multiple tests, we selected an agitation rate of 15 rpm and a duration of coating of 2 hours at 37° C.

3) Adhesion of the Cells on the Microparticles

Different agitation rates and times of the cells in the presence of the microparticles were tested to perfect the conditions of adherences of the cells on the microcarriers. It was thus found that adherence of the PC12 cells was maximized for agitation at 3 rpm for 4 hours at 37° C. in an incubator at 5% $CO_2$.

Figure 2A:
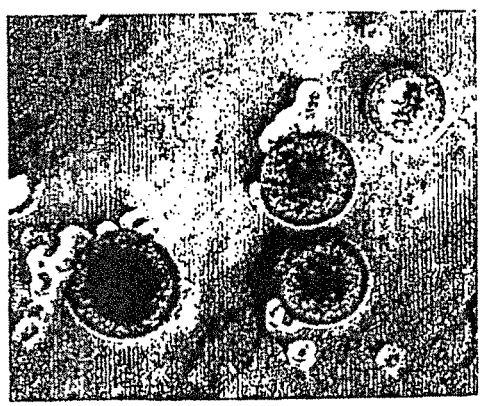
FIG. 2A shows PC12 cells adhered to the MPAs observed by optical microscopy.

The tests of separation of the cells alone from the cells adhered to the microparticles led to centrifuging the microparticle/cell suspension at 135 g for 10 seconds. This processing, as well as the passage of the residue in a 10-μl Hamilton syringe used for the grafts, did not produce a decrease in the number of microparticles having cells on their surface. Under these conditions and after counting under the microscope of the microparticle/cell suspension, it was possible to obtain about 90% of microparticles with cells adhered to their surface. We found, on average, 8 to 10 cells per microcarrier. In contrast, when the microspheres were not coated, only 5% of them had cells adhered to their surface. The coating of the microparticles by a combination of fibronectin-like agent and poly-D-lysine was thus essential to make the cells adhere to them. This adherence was confirmed by scanning electronic microscope images (FIG. 2).

4) Characterization In Vitro

The coating was characterized by atomic force microscopy and showed that the coating was distributed in a homogeneous manner on the particle and diminished the porosity of its surface. Under the previously specified coating conditions, the thickness of the coating was around 20 nm. The coating remained intact after lyophilization and maintained its efficacy of adhesion and differentiation in an in vitro adhesion test.

Under the previously specified adhesion conditions, when $1.5 \times 10^5$ cells were brought into the presence of the MPAs, an average of $5 \times 10^4$ cells adhered on each MPA.

Example 3

Results of the NGF/PC12 MPAs on Animals

The MPAs release NGF in a controlled, prolonged manner. In fact, the initial results of the kinetic of release in vitro showed that for 200 μg of encapsulated NGF, 15% was released in a continuous manner during the first two weeks. The implantation of 0.5 mg of MPAs thus leads to the release of 5-10 ng of NGF per day which is in agreement with the quantities necessary for action of NGF on the cells.

Figure 2B:
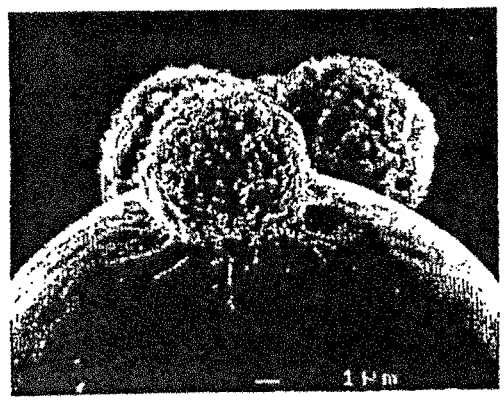
FIG. 2B shows PC12 cells adhered to the MPAs observed by scanning electronic microscopy.
Figure 3:
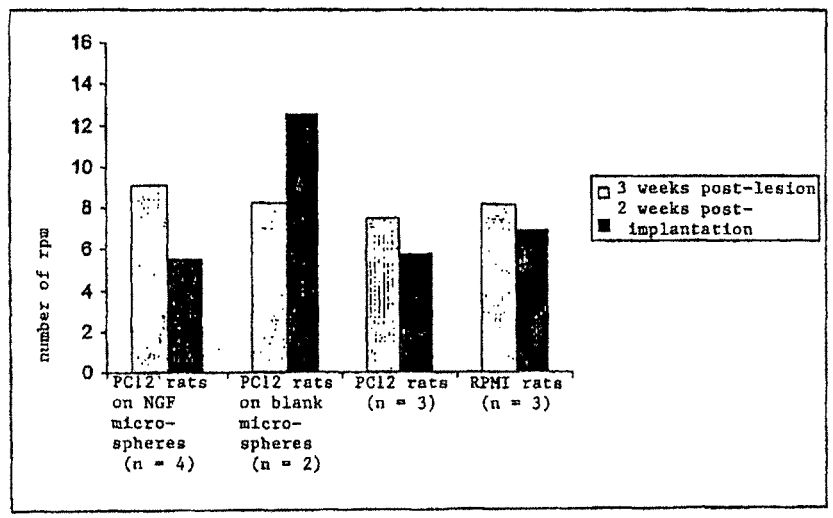
FIG. 3 is a histogram representing the amphetamine-induced rotatory behavior of different groups of rats before and after implantation of: PC12 cells with MPA (thus releasing NGF), PC12 cells with blank microparticles (not releasing NGF), PC12 cells alone or after injection solely of culture medium.
Figure 4:
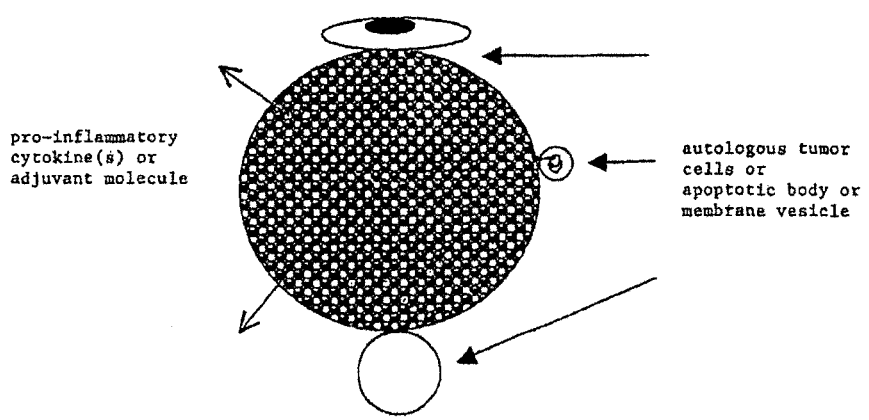
FIG. 4 is a schematic representation of MPA for an antitumor vaccine.

After implementation in the denervated striatum of parkinsonian rats, the PC12 cells remained strongly adhered on the microparticles. The transported cells continued to express tyrosine hydroxylase and were thus capable of producing dopamine. The microparticles still had not degraded and still functioned as cell supports two weeks after implantation. In fact, the microparticles were still spherical and had a rather smooth appearance without vacuolization pores. Generally speaking, the cells adhered to the microparticles with or without NGF had a differentiated appearance compared to the cells grafted unaided in the striatum. Observing these cells at high degrees of magnification, it was noted that on the microparticles releasing NGF, the extensions were longer, comprising more or less 2 to 3 times the size of the cell body (FIG. 2B). At the behavioral level, the initial results of the amphetamine-induced rotation tests showed that only the rats having received the cells with the microparticles releasing NGF had improved (FIG. 3). Among these results it would appear that the PC12 cells adhered to the microparticles not releasing NGF stop proliferating.

Results on Animals

Immunolabeling with an antibody recognizing the active site of NGF two weeks after implantation of the microspheres in the striatum of the parkinsonian rat showed that NGF was clearly released in a biologically active form. At two weeks, NGF was still detected in the MPAs and released all around them in a homogeneous manner and a distance of at least 40 μm. In certain sites around MPAs releasing NGF, axon networks were also observed, clearly demonstrating the release of the growth factor which thereby stimulated the differentiation of the PC12 cells.

PC12 cells, like other cell lines or even stem cells, can form tumors after implantation. Proliferation markers showed that in grafts of PC12 cells adhered to MPAs, there was a decrease in the number of cells that proliferate. This effect was more pronounced with the MPAs releasing NGF.

Cell death by apoptosis was also diminished in the grafting of PC12 cells adhered to MPAs releasing or not releasing NGF.

At the behavioral level, the amphetamine-induced rotation test showed that only the rats having received the cells with MPAs releasing NGF were improved, thereby confirming the efficacy of the MPAs.

Example 4

Preparation of MPAs Releasing GDNF Transporting Dopaminergic (E-Dopa) Embryonic Cells After incubation of MPAs coated with poly-D-lysine with cells at a rotation rate of 6 rpm for a minimum of one hour, E-dopa cells adhered to the surface of 70 to 90% of the MPAs. The number of adhered cells was quite variable, in the range of 5-30 cells per MPA.

Example 5

General Presentation of the MPAs for Antitumor Vaccination

Our clinical experience with antitumor vaccination as well as the results published in the literature confirm that the culture of tumor cells is a limiting step in this type of approach. The yield is low and the elapsed time for obtaining the requisite number of cells is often incompatible with the rapidity of evolution of the tumor. Autologous cells still remain the most suitable source of specific tumor antigens (STAs) whether for loading dendritic cells in vitro or subcutaneous vaccination. It is therefore useful to develop a system that can be prepared rapidly from a small number of cells capable of presenting the majority of tumor antigens as well as an adjuvant of the dendritic cells.

We formulated for this bio-artificial particles based on the concept of the pharmacologically active microcarriers (MPAs) ERIT-M 0104 developed at INSERM. These are microspheres with a diameter of approximately 5 to 30 μm, constituted of a biodegradable, biocompatible copolymer (such as poly[lactic acid-co-glycolic acid] or PLGA) that can release in a controlled, prolonged manner an adjuvant such as a pro-inflammatory cytokine (such as GM-CSF, IL2, IL12 or IL18). Due to their surface properties (film-coated by synthetic cell adhesion molecules), these microparticles can carry on their surface tumor antigens prepared from autologous tumor cells (membrane vesicles, apoptotic bodies, exosomes, protein extract, mRNA and DNA).

These MPAs carrying tumor antigens on their surface and releasing in a controlled manner an adjuvant such as a cytokine, may be:
- brought into contact with dendritic cells in vitro (in the framework of vaccination with dendritic cells obtained from blood stem cells), or
- administered to a patient directly via the subcutaneous, intradermal or intramuscular route.

The immunogenic character of the MPA is due not only to the combination with the tumor antigen and the prolonged release of cytokine, but also to the presentation of the antigen on a microparticle system. This is an ideal mode of presentation for the recognition of the antigen by the dendritic cells. This nonspecific immune stimulation or the adjuvant role of the microparticles has been demonstrated for a long time (Mescher and Rogers, 1996; Mescher and Savelieva, 1997; Nakaoka et al., 1995; Rogers and Mescher, 1992; Scheicher et al., 1995a, 1995b; Venkataprasad et al., 1999).

PLGA microspheres were already described as being able to release immunostimulant and/or antitumor cytokines (Golumbek et al., 1993; Mullerad et al., 2000; Pettit et al., 1997) and we have already demonstrated our capacity in the laboratory to develop microspheres releasing antitumor agents or recombinant proteins (Menei et al., 1996, 1999, 2000; Nan et al., 2000).

Example 6

MPA Carriers of Plasma Membranes in Antiglioma Vaccination

The PLGA microspheres used (with and without GM-CSF, an activating cytokine) were prepared by the solvent evaporation technique as previously described (Menei et al., 1993; Menei et al., 1996; Péan et al., 2000). Filtration was used to select the smallest microspheres (5 to 30 µm in diameter).

Purification of the plasma membranes of the GS-9L cells was performed by incubating $1.5 \times 10^8$ cells for 15 minutes at 4° C. in a hypotonic buffer (KCl 42 mM, Hépes 10 mM pH 7, $MgCl_2$ 4.5 mM and 1% of protease inhibitors) by performing about 50 passages in a 30-gauge syringe. The cells broken in this manner were then centrifuged (250 g; 10 minutes; 4° C.) to separate the membranes in the supernatant, the non-lysed cells and the nuclei collected in a residue. The membranes were then recovered after an ultracentrifugation step (100,000 g; 90 minutes; 4° C.). They were then placed in a biphasic polyethylene glycol (PEG 8000)/Dextran T500 system equilibrated 48 hours in advance and then centrifuged (3000 g; 15 minutes; 4° C.).

The plasma membranes were then arranged at the interphase of the biphasic system by affinity for the two phases. After recovery, 2 washings in a sucrose 0.25 M, Tris HCl 1 M buffer were performed (100,000 g; 30 minutes; 4° C.). The membranes were stored in this same buffer at −80° C. until their use. Among the adsorption and formulation protocols tested, that which seemed to be the most effective brought together the membranes and the microspheres without prior coating in the Tris pH 6.8 buffer. Other adsorption protocols optimal for protein fractions, membrane vesicles, apoptotic bodies and exosomes are under development. These protocols were validated by radiotagging the protein fraction by $I^{125}$ by direct immunofluorescence of membrane markers in confocal microscopy then by analysis of the enzymatic activity of the adsorbed structures.

Example of adsorption of the plasma membranes of GS-9L cells on PLGA microspheres: The purified plasma membrane preparation was treated by sonication for 30 seconds to reduce the size of the aggregates of membrane vesicles. The equivalent of 10 µg of membrane proteins was then brought into the presence of 20,000 PLGA microspheres. This was then placed under rotation (60 rpm) overnight at 4° C.

Quantitative determination using Lowry's test was performed to determine the amount of membrane proteins recovered. Using a calibration range of BSA (comprised between 0.2 and 1 µg/µl), the protein concentration of the samples was calculated. The aliquot, called the initial aliquot (Ai), collected at the beginning of purification (just after lysis) and containing all of the proteins of the cell, had a protein concentration between 7000 and 10,000 µg/ml. In contrast, at the end of enrichment, we obtained a protein concentration comprised between 200 and 300 µg/ml. We thus recovered 3% of the total proteins.

The profile of the isolated proteins was analyzed by polyacrylamide gel migration showing an intermediary migration profile of the profiles of the soluble and insoluble fractions of the cell lysates. It was the insoluble fraction that contained the majority of the membrane proteins. The determination of the specific activity of 5'-nucleotidase and of Fas-ligand by Western blot indicated an enrichment of these membrane proteins, proving the membrane nature of the enriched material. Direct immunofluorescence of membrane markers with confocal microscopy (5'-nucleotidase, integrin, ICAM-1) confirmed fixation of the membrane proteins on the microparticles.

The invention claimed is:

1. A method of repairing tissue comprising implanting into a patient a therapeutically effective amount of a pharmaceutical composition comprising
    microparticles comprising a biodegradable and biocompatible material having cells of interest adhered to at least a portion of a surface of the microparticles, wherein the biodegradable and biocompatible material comprises an adhesive coating that facilitates adhesion of the cells, and wherein the cells of interest are selected from the group consisting of embryonic cells and stem cells; and
    at least one substance active on the cells or their environment upon implantation of the microparticles in the patient wherein the substance is released in a controlled or extended manner for at least two weeks after implantation,
    wherein the substance is a factor acting in cell differentiation and/or a factor promoting the survival of cells,
    wherein the microparticles have a diameter of about 10 to about 500 µm, and
    wherein the biodegradable and biocompatible material comprises polyester.

2. The method of claim 1, wherein the at least one substance is located on the surface of and/or incorporated in the microparticles.

3. The method of claim 1, wherein the polyester is a poly(α-hydroxyacid).

4. The method of claim 3, wherein the poly(α-hydroxyacid) is a polyactide or a polylactide co-glycolide.

5. The method of claim 1, wherein the polyester is a poly ε-caprolactone.

6. The method of claim 1, wherein the adhesive coating on the material is a compound selected from the group consisting of a compound bearing a RGD sequence, poly-D-lysine, poly-L-lysine, poyornithine, polyethylene amine, a fibronectin, a compound belonging to the extracellular matrix, and a mixture thereof.

7. The method of claim 1, wherein the substance is a growth factor.

8. The method of claim 7, wherein the growth factor is selected from the group consisting of NGF, BNDF, NT-3, TGFβs, the GDNF family, FGFs, EGF, and PDGF.

9. The method of claim 1, wherein the stem cells are neural stem cells or mesenchymal stem cells (MSC).

* * * * *